United States Patent [19]
Pojer et al.

[11] Patent Number: 5,501,708
[45] Date of Patent: Mar. 26, 1996

[54] PROCESS FOR TANNING HIDES AND COMPOUNDS FOR USE THEREIN

[75] Inventors: Peter Pojer, North Caulfield; Kenneth C. Montgomery, North Warrandyte; Chi P. Huynh, Hawthorn; Brian Milligan, North Balwyn, all of Australia

[73] Assignee: Commonwealth Scientific and Industrial Research Organisation, Campbell, Australia

[21] Appl. No.: 129,181

[22] PCT Filed: Apr. 9, 1992

[86] PCT No.: PCT/AU92/00154

§ 371 Date: Oct. 7, 1993

§ 102(e) Date: Jan. 18, 1994

[87] PCT Pub. No.: WO92/18456

PCT Pub. Date: Oct. 29, 1992

[30] Foreign Application Priority Data

Apr. 9, 1991 [AU] Australia ................................. PK5510
Feb. 18, 1992 [AU] Australia ................................. PL0950

[51] Int. Cl.$^6$ ........................... C14C 3/06; C14C 3/08
[52] U.S. Cl. ...................... 8/94.26; 8/94.27; 8/94.29; 8/94.33; 252/8.57
[58] Field of Search ........................ 549/242, 245; 560/89, 67, 51; 252/8.57; 8/94.26, 94.27, 94.29, 94.3, 94.32, 94.33

[56] References Cited

U.S. PATENT DOCUMENTS

| | | | |
|---|---|---|---|
| 3,022,287 | 2/1962 | Mench et al. | 536/63 |
| 3,183,246 | 5/1965 | Hirsch et al. | |
| 3,183,248 | 5/1965 | Hirsch et al. | 549/242 |
| 3,423,162 | 1/1969 | Papayannis et al. | 8/94.29 |
| 3,459,733 | 8/1969 | Byrd, Jr. et al. | 536/18.2 |
| 4,101,271 | 7/1978 | Bockelman et al. | 8/94.26 |
| 4,379,886 | 4/1983 | McLaughlin et al. | 525/162 |
| 4,472,466 | 9/1984 | Kelly et al. | 427/393.4 |
| 4,902,816 | 2/1990 | McDaniel | 560/88 |

FOREIGN PATENT DOCUMENTS

| | | |
|---|---|---|
| 1002190 | 8/1969 | United Kingdom . |
| 1222575 | 2/1971 | United Kingdom . |
| 1588047 | 4/1981 | United Kingdom . |

OTHER PUBLICATIONS

Morrison et al., *Organic Chemistry*, 1983, pp. 1079–1080 and 1104. (Month Unknown).
Morrison et al, *Organic Chemistry*, 1983, 819–820. (Month Unknown).
Derwent Abstract Accession No. 83–7200334/30 dated Jun. 20, 1983.
Derwent Abstract Accession No. 83–767128/38 dated Feb. 25, 1983.
Derwent Abstract Accession No. 84–217121/35 dated Jul. 24, 1984.
Derwent Abstract Accession No. 86–186048/29 dated Jun. 5, 1986.
Derwent Abstract Accession No. 88–165732/24 dated May 10, 1963.
Derwent Abstract Accession No. 86–186048/29 dated Jun. 5, 1986.
Derwent Abstract Accession No. 88–238133/24 dated Jul. 14, 1988.
Patent Abstracts of Japan C–194, p. 147, No. JP,A, 58–140046, dated Aug. 19, 1983.
Patent Abstracts of Japan C–194, p. 147, No. JP,A, 58–140047, dated Aug. 19, 1983.
Patent Abstracts of Japan C–194, p. 147, No. JP,A, 58–140048, dated Aug. 19, 1983.
Patent Abstracts of Japan C–109, p. 10, No. JP,A,57–38749 dated Mar. 3, 1982.
Patent Abstracts of Japan C–109, p. 10, No. JP,A,57–38750 dated Mar. 3, 1982.

*Primary Examiner*—Prince Willis, Jr.
*Assistant Examiner*—Alan D. Diamond
*Attorney, Agent, or Firm*—Merchant, Gould, Smith, Edell, Welter & Schmidt

[57] ABSTRACT

An organic polyol ester of a polycarboxylic acid having formulae (Para) and/or (Meta) and/or (Ortho), wherein $R_6$ is —(COOR$_1$)x, or (I)$_1$R$_7$ is H; or $R_6$ and $R_7$ together for (II); $R_1$ and $R_2$ are hydrogen or —OR$_1$ and —OR$_2$ together form an anhydride (—O—) bond; x is an integer of 0 or 1; Z is an integer ranging from 1 to the number of hydroxy groups on the polyol and D is a polyol residue. Also disclosed are processes for the preparation of these polyol esters, a tanning composition comprising a metallic salt and a polyol ester, and a method of tanning using said composition.

11 Claims, No Drawings

PROCESS FOR TANNING HIDES AND COMPOUNDS FOR USE THEREIN

This application is a 371 of PCT/au92/00154 filed Apr. 9, 1992.

The present invention relates to a process for the preparation of tanned leather which utilises metals other than chromium, and to compounds for use in such a process.

Leather is a material which is sensitive to heat when in a wetted state and may be subject to marked shrinkage which may occur abruptly over a relatively narrow temperature range. The temperature which marks the onset of such shrinkage is known as the shrinkage temperature. The shrinkage temperature differs according to the type of tanning material used and is thus used to characterise a particular type of leather. In general terms, the highest degree of hydrothermal stability is customarily obtained with chrome tanning agents. However, chrome tanning agents generate pollution problems due to the effluent generated. Concerns as to the carcinogenic nature, of chromium (VI) compounds have lead to the introduction of chrome content restrictions for industrial effluent.

Significant research has been initiated in the prior art to develop a non-chrome tanning system which will produce leather characteristics at least comparable with chrome leathers. Aluminium tanning systems have been tried, however such systems suffer from three disadvantages. Firstly, aluminium binds to collagen over a very narrow pH range which is close to the precipitation point of the tanning salt. Secondly, the maximum shrinkage temperature obtainable with aluminium alone in the prior art has been approximately 80° C. This may be compared with chrome tanned leathers having shrinkage temperatures of between approximately 100° C. and 125° C. Thirdly, aluminium tanned products deteriorate due to the fact that the aluminium may migrate out of the leather and is thus generally unstable over time. During wool skin dyeing for example, aluminium removal is a particular problem.

Attempts have been made in the prior art to overcome these difficulties. For example, in GB Patent Application 2,153,844, it has been proposed to tan hides and skins using a basic aluminium salt and a polycarboxylic acid of, benzene containing three or more carboxylic acid groups. Whilst such additives have improved hydrothermal stability somewhat, leathers produced by such techniques are still substantially inferior to chrome leathers and still suffer from significant deterioration over time due to aluminium depletion.

Accordingly, it is an object of the present invention to overcome, or at least alleviate, one or more of the difficulties related to the prior art.

Accordingly, in a first aspect of the present invention, there is provided a process for the preparation of tanned leather, which process includes providing
- a skin or hide;
- an effective amount of a metallic salt, wherein the metal is selected from chromium, aluminium, titanium or zirconium; and
- at least one organic polyolester of a hydroxycarboxylic or polycarboxylic acid or derivative thereof;

treating the skin or hide with the organic polyol ester; and contacting the treated skin or hide with the metallic salt for a period sufficient to complex therewith.

The leathers produced according to the process of the present invention may be characterised by improved hydrothermal stability as measured by an increase in shrinkage temperature. The leather produced according to the process of the present invention may further be characterised by an excellent light fastness of the leather.

The skin or hide to be treated may be of any suitable type. The skin or hide may be obtained from an ovine, porcine, bovine or caprine animal, An ovine skin such as a wool skin is preferred. The skin or hide may be pre-treated in any manner known per se, to prepare the hide for the tanning process. A green hide may be used. The hide may be pickled hide. A pickled woolskin is preferred.

However the process of the present invention may also be applied to a delimed hide, for example a delimed sheepskin pelt. It is accordingly unnecessary to submit the hide to a pickling and salt treatment step. This may reduce effluent and corrosion problems.

The metallic salt utilised to treat the skin or hide, as stated above, may be a chromium, aluminium, titanium or zirconium salt. Preferably an aluminium, titanium or zirconium salt is used. An aluminium salt is preferred. Basic aluminium basic chloride, aluminium sulphate, aluminium formate or aluminium acetate may be used. Aluminium sulphate is preferred.

The metallic salt may be utilised in any suitable effective amount. The metallic ion may be present in amounts of from approximately 0.25% to 10% by weight based on the moist weight of green hide. Preferably the metal, e.g. aluminium ion is present in amounts of approximately 0.5% to 8% by weight. The metallic, e.g. aluminium salt may be introduced in the form of a solution. An organic or aqueous solution may be used. An aqueous solution is preferred.

The hide may be contacted with the metallic salt for a period sufficient to permit binding of the metallic ions to the hide. Contact may continue for approximately 1 to 5 hours, preferably 2 to 4 hours.

The at least one organic polyolester of a polycarboxylic or hydroxycarboxylic acid may be of any suitable type. A polyol ester of gallic acid, phthalic acid, 3,3', 4,4' benzophenone tetracarboxylic acid, pyromellitic acid or trimellitic acid may be used. A polyolester of trimellitic acid is preferred. The polyolesters of trimellitic acid may exhibit superior light fastness relative to equivalent gallic acid esters. A sugar or polysaccharide ester is preferred. The polyol esters may be derived from mannitol, sorbitol, glucose, sucrose, lactose, pentaerythritol di-pentaerythritol, or tri-pentaerythritol. Particularly preferred polyol esters may be selected from one or more of the ortho(o-), meta(m-) and para(p-) forms of pentaerythritol tetra(trimellitate)

pentaerythritol tetrapyromellitate polyol esters of pentaerythritol and 3,3', 4 4' benzophenone tetracarboxylate sorbitol hexa(trimellitate)

mannitol hexa(trimellitate)

glucose pentaphthalate glucose penta(trimellitate)

sucrose octaphthalate sucrose octa(trimellitate)

sucrose octagallate lactose octa(trimellitate)

lactose octagallate

The polyolesters may be present in any isomeric form.

The at least one organic polyol ester of polycarboxylic acid or hydroxycarboxylic acid may be present in any suitable amounts. The organic polyol esters may be present in amounts of from approximately 1% by weight to 20% by weight, preferably 5% to 15% by weight, based on the moist weight of green hide to be treated. The organic polyolester may be provided in a solution. An aqueous or organic solution may be used. An aqueous solution is preferred. An aqueous solution buffered to a pH of approximately 2.5 to 5 is preferred.

Whilst the mechanism of reaction is not known, it is postulated that the organic polyol esters increase the number of potential binding sites for the metallic ions. Accordingly, the organic polyol esters may be contacted with the hide or skin for a period sufficient for reaction to take place therebetween. A period of approximately 1 to 24 hours, preferably 5 to 10 hours, has been found to be suitable.

The contact steps may be conducted sequentially. However where the organic polyol esters are esters of gallic acid, the contact steps with organic polyolesters may be conducted simultaneously with the contacting step utilising the metallic salts.

It will be understood that a number of the organic polyolesters of polycarboxylic acids useful in the process according to the present invention are novel per se. Accordingly, in a further aspect of the present invention there is provided an organic polyolester of a polycarboxylic acid having the formula

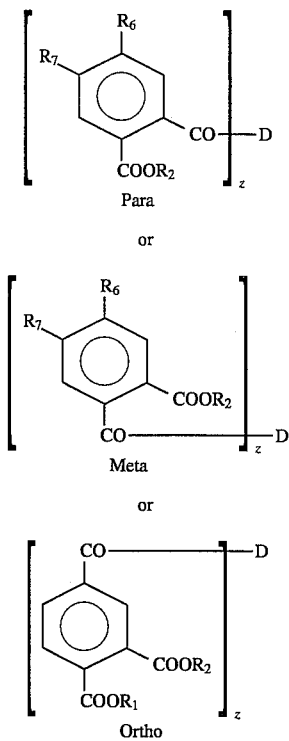

wherein $R_6$ is H or $-(COOR_1)_x$, or

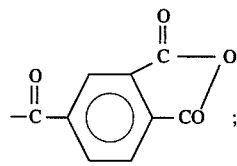

$R_7$ is H or $-COOR_1$; or $R_6$ and $R_7$ together form

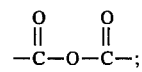

$R_1$ and $R_2$ are hydrogen or $-OR_1$ and $-OR_2$ together form an anhydride ($-O-$) bond; x an integer of 0 or 1 provided that where $R_7$ is H, x is 1; z is an integer between 1 and the number of hydroxy groups on the polyol; and D is a residue of a polyol having at least 4 ($-OH$) groups. The polyol residue may be a sugar or polysaccharide moiety or

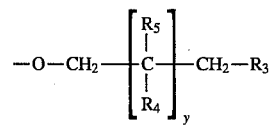

y is 0 or an integer of 1 or greater; $R_3$, $R_4$ and $R_5$, which may be same or different, are selected from hydrogen, hydroxyl, alkyl having 1 to 20 carbon atoms, hydroxy alkyl having 1 to 20 carbon atoms, or a radical of the formula

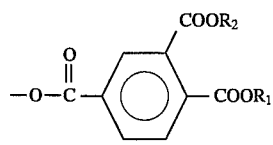

wherein $R_1$ and $R_2$ are described above, or mixtures thereof.

Preferably x is 1. More preferably y is an integer of 1 to 6.

It will be understood that the organic polyol esters of this aspect of the present invention include ortho(o-), meta(m-) and para(p-) isomeric forms of the organic polyolesters of the present invention.

The organic polyol esters may be selected from o-, m- and p- forms of pentaerythritol tetra(trimellitate)

pentaerythritol tetrapyromellitate polyol esters of pentaerythritol and 3,3',4,4' benzophenone tetracarboxylate sorbitol hexa(trimellitate)

mannitol hexa(trimellitate)

glucose pentaphthalate glucose penta(trimellitate)

sucrose octaphthalate sucrose octa(trimellitate)

sucrose octagallate lactose octa(trimellitate)

lactose octagallate.

It has been found that the o-, m- and p- isomeric forms of the organic polyolesters may also function in the process of the present invention to significantly increase the shrinkage temperature of the tanned leather.

The shrinkage temperature may be increased to 100° C. or greater to provide a boil proof leather.

In a further aspect of the present invention there is provided a process for the preparation of an organic polyolester of a polycarboxylic acid having the formula

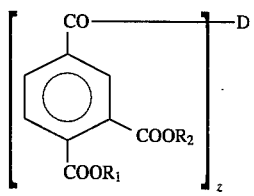

wherein $R_1$, $R_2$, z, and D are as described above, which process includes
providing
a polycarboxylic acid anhydride of the formula

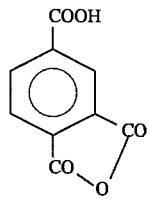

and a polyol selected from a polysaccharide, a sugar or a compound having the formula

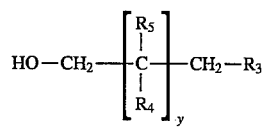

wherein y is 0 or an integer of 1 or greater, $R_3$, $R_4$ and $R_5$ are selected from hydrogen, hydroxyl, alkyl having 1 to 20 carbon atoms, hydroxyl alkyl having 1 to 20 carbon atoms, or a radical of the formula

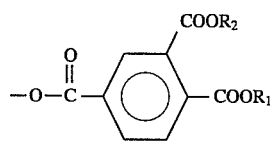

wherein $R_1$ and $R_2$ are as described above;
converting the polycarboxylic acid anhydride to an acid chloride; and
contacting the halogenated acid anhydride with the polyol for a period sufficient to permit reaction therebetween.

The trimellitic acid anhydride may be converted to the acid chloride in known manner. Thionyl chloride, phosphorous oxychloride, phosphorous pentachloride or the like may be used. The polyol may be selected from ethylene glycol, glycerol, pentaerythritol, sorbitol, mannitol, sucrose, lactose and glucose.

The reaction between the trimellitic anhydride acid chloride and the polyalcohol may be conducted under basic conditions. The reaction may continue for approximately 30 minutes to 4 days, depending on heat of reaction chosen.

The acid anhydride polyester so formed may be converted to the dicarboxylic acid in known manner. The compound may be left open to the atmosphere for an extended period. The compound thus takes up water from the atmosphere.

Alternatively, the compound may be treated with water, optionally in the presence of a small amount of acid or alkali.

In a still further aspect of the present invention there is provided a process for the preparation of an organic polyolester of a polycarboxylic acid having the formula

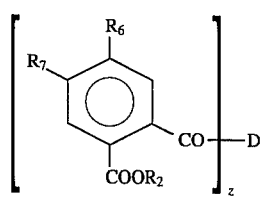

or

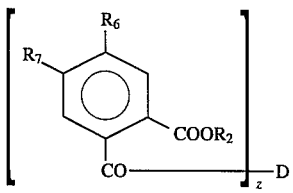

wherein $R_1$, $R_2$, $R_6$, $R_7$, D, z and x are as described above, which process includes
providing a polycarboxylic acid anhydride of the formula

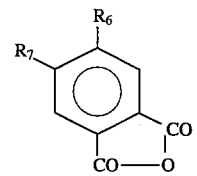

wherein $R_6$ is H or $-(COOR_1)_x$, or

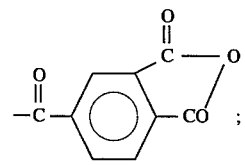

$R_7$ is H or $-COOR_1$; or $R_6$ and $R_7$ together form

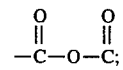

x is 0 or 1 provided that where $R_7$ is H, x is 1; and
a polyol selected from a polysaccharide, a sugar or a compound having the formula

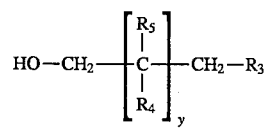

wherein y is 0 or an integer of 1 or greater, $R_3$, $R_4$ and $R_5$ are selected from hydrogen, hydroxyl, alkyl having 1 to 20 carbon atoms, hydroxy alkyl having 1 to 20 carbon atoms, or a radical of the formula

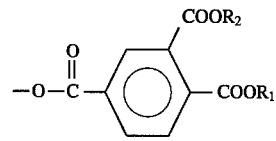

wherein $R_1$ and $R_2$ are as described above; and contacting the polycarboxylic acid anhydride with the polyol at elevated temperature for a period sufficient to permit reaction therebetween.

The reaction mixture may be heated to a temperature in the range of approximately 50° C. to 300° C., preferably 100° C. to 200° C.

The polyol may be selected from ethylene glycol, glycerol, pentaerythritol, sorbitol, mannitol, lactose, sucrose and glucose.

It will be understood that this process provides a much simplified preparative technique for the organic polyolesters of the present invention. The process according to this aspect of the present invention may be conducted in liquid phase, e.g. in solution, preferably a non-aqueous solution. It will also be understood that where two anhydride groups are present in the polycarboxylic acid anhydride, esters can be formed which correspond to the esters detailed herein but have more ester or polycarboxylic groups. Such esters and their production are also within the scope of the present invention.

The process may be conducted in the solid phase, preferably at temperatures of about 150° C. to 200° C.

In a further aspect of the present invention, there is provided a tanning composition including an effective amount of a metallic salt, wherein the metal is selected from chromium, aluminium, titanium or zirconium; and at least one organic polyolester of a hydroxycarboxylic or polycarboxylic acid or derivative thereof.

The metallic salt may be present in amounts of from approximately 5 to 50% by weight, preferably 5 to 15% by weight, based on the total weight of the tanning composition. A chromium, titanium, aluminium or zirconium salt may be used. An aluminium salt is preferred.

The at least one organic polyolester of a hydroxycarboxylic or polycarboxylic acid may be present in amounts of from approximately 50% to 95% by weight, preferably 85% to 95% by weight, based on the total weight of the tanning composition. The polyolesters may be selected from one or more of pentaerythritol tetra(trimellitate)

pentaerythritol tetrapyromellitate polyol esters of glycerol and 3,3',4,4' benzophenone tetracarboxylate sorbitol hexa(trimellitate)

mannitol hexa(trimellitate)

glucose penta(trimellitate)

sucrose octa(trimellitate)

sucrose octagallate lactose octa(trimellitate)

lactose octagallate

The organic polyol esters may be utilised in any suitable isomeric form. The trimellitate esters are preferred.

The tanning composition may be provided in the form of a solution. An organic or aqueous solution may be used.

The tanned leathers formed according to the process of the present invention may be subjected to further compounding steps as required. For example, the tanned leather so formed may be subjected to a dyeing process. The tanned leather according to the present invention exhibits moderate to good dye bath stability. Leathers tanned with trimellitate esters may exhibit good dye bath stability.

Other compounding ingredients which may be utilised in the process of the present invention include agents which may improve the light fastness of the tanned leathers. Addition of such light fastness agents is preferred where the organic polyesters are organic polyesters of gallic acid. The light fastness agents may include anti-oxidants, free radical scavengers and UV absorbers.

The present invention will now be more fully described with reference to the accompanying examples. It should be understood, however, that the description following is illustrative only and should not be taken in any way as a restriction on the generality of the invention described above.

EXAMPLE 1

Preparation of organic polyol esters

Trimellitic acid anhydride (3 g) is dissolved in dimethyl formamide (DMF). A polyol, pentaerythritol (0.5 g) is added and the mixture heated at approximately 200° C. for 2 hours. The reaction product, a mixture of m- and p- isomers of pentaerythritol tetra(trimellitate), designated Siraltan-P, below.

Lamb Intestines

Siraltan-P (0.5 g) was dissolved in aqueous alkali buffer and pH was adjusted to approximately 3.5.

This mixture was added to lamb intestines (1 g). pH was adjusted to approximately 2.8 utilising a mixture of formic acid and sulphuric acid. The mixture was shaken 2 hours and left overnight. The intestines were washed with water.

To the treated intestines was added an aqueous solution of approximately 4.5% aluminium sulphate solution. pH was adjusted to approximately 4–4.1 with sodium carbonate. The intestines were washed with water.

Similarly, the process was repeated utilising sucrose octaphthalate (Siraltan-PH).

Results are set out in Table 1 below.

EXAMPLE 2

Tanning Pickled Sheepskin Pelt

Pickled pelt (wet weight 450 g) was treated with an aqueous solution (48 hours, pH 4.6) of SIRALTAN-S (sucrose octa-trimellitate isomeric mixture) (54 g, 12%). After drumming for 2 hours the mixture was acidified with 1:1 aqueous formic acid (65 ml) to pH 2.85. The mixture was drummed overnight, drained and the pelt washed with water.

The pelt was drummed with a solution of aluminium sulphate (135 g) in water (1l) for 4 hours. It was then slowly basified to approximately pH 4.05 with 20% aqueous sodium carbonate solution (210 ml), drummed 4 hours and allowed to stand overnight. It was then drained and washed with water, shrinkage temperature 91° C. Results are set out in Table 1 below.

EXAMPLE 3

When the pelt (450 g) was reacted with SIRALTAN-S (72 g, 16%) as above, subsequent acidification, washing and aluminium re-tannage gave leather of shrinkage temperature 101° C. Results are set out in Table 1 below.

EXAMPLE 4

Wool-on Skin

The pickled wool-on skin (450 g) was drummed overnight with an aqueous solution (900 ml) of SIRALTAN-S (22.5 g, pH 4.6). It was then acidified with 1:1 formic acid as before, drained and washed.

Aluminium re-tannage was performed as before to give a shrinkage temperature of 86° C. Results are set out in Table 1 below.

leather of shrinkage temperature 93° C. Results are set out in Table 1 below.

EXAMPLE 7

Tannage with Siraltan-B (Sorbitol hexatrimellitate isomeric mixture)

Pickled sheepskin pelt (2.5 g) was shaken with an aqueous solution (24 ml) of SIRALTAN-B (0.84 g, pH 4.5). Acidification, washing and aluminium re-tannage as before gave leather of shrinkage temperature 92° C. Results are set out in Table 1 below.

TABLE 1

| Tanning Substance | Collagen Substrate | Quant. % w/wt | Aluminium Sulphate $Al_2O_3$ | Shrinkage Temp. (Approx) | Tannage Stability | Handle | Leather Colour (undyed) | Dye Colour Quality |
|---|---|---|---|---|---|---|---|---|
| 1. SIRALTAN-PH | Lamb intest. | 16% | 4.5% | 85° C. | Moderate | Full, firm | White | — |
| 2. SIRALTAN-P | Lamb intest. | 45% | 4.5% | >115° C. | V. good | Full, firm | White | — |
|  | Lamb intest. | 30% | 4.5% | 90° C. | Good | Full, firm | White | — |
|  | Lamb intest. | 16% | 4.5% | 78° C. | Moderate | Full, firm | White | — |
|  | Pickled pelt | 32% | 4.5% | 75° C. | Moderate | Full, firm | White | — |
| 3. SIRALTAN-B | Pickled pelt | 34% | 4.5% | 92° C. | Good | Full, firm | White | — |
|  | Pickled pelt | 20% | 4.5% | 76° C. | Moderate | Full, firm | White | — |
| 4. SIRALTAN-S | Pickled pelt | 30% | 4.5% | >100° C. | Excell. | Very full | White | Bright |
|  | Pickled pelt | 10% | 4.5% | 82° C. | Good | Full | White | — |
|  | Pickled hide (2 mm thick) | 22% | 4.5% | >100° C. | Excell. | Very full | White | Bright |
|  | Pickled hide | 14% | 4.5% | 90° C. | Excell. | Very full | White | — |
|  | Pickled pelt | 16% | 4.5% | 97° C. | V. good | Very full | White | Bright |
|  | Pickled pelt | 14% | 4.5% | 90° C. | V. good | Very full | White | Bright |
|  | Pickled pelt | 12% | 4.5% | 91° C. | V. good | Very full | White | Bright |
|  | Pickl. kangaroo | 14% | 4.5% | 84° C. | V. good | Very full | White | — |
|  | Pickled wool on skin | 5% | — | 80° C. | V. good |  |  |  |

Note:
(1) SIRALTAN-PH is a sucrose octaphthalate carboxylate form of ethylene glycol diphthalate.
(2) SIRALTAN-P, SIRALTAN-B and SIRALTAN-S are m-, p- carboxylate forms of pentaerythritol penta(trimellitate), sorbitol hexa(trimellitate) and sucrose octa(trimellitate) respectively.

The results achieved in Table 1 may be contrasted with comparative results for chromium tannage in Table 2.

TABLE 2

| Tanning Substance | Quant. % w/wt | Retannage (syntan) | Offer % w/wt | Shrinkage Temp. | Tannage Stability | Handle | Leather Colour (undyed) | Dye Colour Quality |
|---|---|---|---|---|---|---|---|---|
| Chromium | 7% | Basynton-D | 10% | 100° C. | Excellent | Firm, quite full | L/green | Dull |
|  |  | Regulan RV | 3% |  |  |  |  |  |

EXAMPLE 5

Kangaroo Skin

Pickled kangaroo skins (1.6 kg) were drummed overnight with an aqueous solution (1.5 l) of SIRALTAN-S (225 g, pH 4.6). Acidification, wash, re-tannage with aluminium sulphate as before gave-tanned skins of shrinkage temperature 84° C. Results are set out in Table 1 below.

EXAMPLE 6

Tanning Hide

Pickled split hide pieces (3.8 kg) were drummed with an aqueous solution (4 l) of SIRALTAN-S (524 g) as before. Acidification, washing and aluminium re-tannage gave

EXAMPLE 8

Lamb Intestines (Model system)

Ethylene glycol di(trimellitate) (0.5 g) was dissolved in a salt/acetate buffer (pH 4.6) and pH was adjusted to 4.6. Volume was adjusted to 50 ml with the buffer. This mixture was added to dried lamb intestines (1 g) and mixture shaken 2 hours and left overnight. The intestines were washed with water and shrinkage temperature measured. (Ts~62°; control Ts~57°). To the treated intestines was added a 0.05M aluminium sulphate solution of which the pH has been adjusted to 3.95 to 4.0. The mixture was shaken for 2 hours and left overnight. The intestines were washed with water (Ts=84°; control=83°).

Similarly, the following compounds were examined and shrinkage temperatures at which protein denatures determined.

|  | Ts No Al | Ts After Al Treat. |
|---|---|---|
| control, gallic acid, trimellitic acid | 57° | 80° |
| methyl trimellitate | 60° | 81° |
| methyl gallate | 60° | 81° |
| ethylene glycol di(trimellitate) | 60° | 81° |
| ethylene glycol digallate | 60° | 94° |
| glycerol tri(trimellitate) | 60° | 81° |
| glycerol trigallate | 69° | 103° |
| pentaerythritol tetra(trimellitate) | 67° | 87° |
| pentaerythritol tetragallate | 65° | 92° |
| sorbitol hexa(trimellitate) | 66° | 87° |
| sorbitol hexagallate | 71° | 104° |
| mannitol hexa(trimellitate) | 67° | 89° |
| mannitol hexagallate | 72° | 103° |
| glucose penta(trimellitate) | 65° | 85° |
| glucose pentagallate | 77° | 110° |

Tannage via the gallates can be performed in a concurrent process rather than a sequential one as described above.

Thus, the intestine pieces and mannitol hexagallate ester were mixed together in water and the aluminium solution was added at pH 2.5 (the pH of the aluminium solution). The pH was gradually raised to 3.4 with base at which point the intestines were left overnight. They were then washed. Ts~100°.

EXAMPLE 9

Pickled (pH 3) sheepskin pelt (3 g) was mixed with a solution of glycerol trigallate (0.3 g) in the buffer pH 4.6( 50 ml). After 2 hours the mixture was allowed to stand overnight, then washed with water (Ts~65°) and treated with 0.05M aluminium sulphate solution pH 4.0 (50 ml). After 2 hours mixing, the mixture was allowed to stand overnight, washed with water. Ts~94°)

EXAMPLE 10

Pickled (pH 3) sheepskin pelt (3 g) was treated with glucose penta(trimellitate) (0.3 g) dissolved in buffer pH 4.6 (50 ml) and after treatment analogous to that above, a leather was obtained Ts~88°.

EXAMPLE 11

Stability in Dye-Bath Conditions

Dye-bath conditions were: pH 3.1 aqueous formic acid, temperature 60° C. Tanned leather samples were shaken under these conditions and portions were removed regularly for shrinkage temperature determinations. pH was adjusted to 3.1, if necessary, with dilute formic acid.

Leather tanned with a combination of mannitol hexagallate and aluminium gave the following results

| Time in Bath | Ts |
|---|---|
| 0 hours | 103° |
| 1 hour | 98° |
| 2 hours | 100° |
| 4 hours | 92° |
| 6 hours | 96° |

Leather tanned with a combination of mannitol hexa(trimellitate) and aluminium gave the following results

| Time in Bath | Ts |
|---|---|
| 0 hours | 89° |
| 1 hour | 88° |
| 2 hours | 86° |
| 3 hours | 77° |
| 5 hours | 78° |
| 6 hours | 79° |

Leather tanned with aluminium alone gave the following results

| Time in Bath | Ts |
|---|---|
| 0 hours | 79° |
| 1 hour | 77° |
| 2 hours | 74° |
| 3 hours | gelly < 60° |

Stability to possible dye bath conditions was further tested as follows

The retanned sheepskin or intestine pieces from pretreatment or control processes were treated in aqueous solution of formic acid at pH 3.2–3.3 at 60° C. for 6 hours. Samples were removed for shrinkage temperature measurements.

EXAMPLE 12

Sheep intestine with a pretan offer of 60% on dry weight.

| CONDENSTATE DETAILS | | | Ts (°C.) after |
|---|---|---|---|
| ANHYDRIDE USED | ALCOHOL USED | MOLAR PROPORTION | retannage with aluminium and washing |
| PMA | Ethylene Glycol | 3:1 | 84 |
| PMA | Glycerol | 4:1 | 87 |
| PMA | Pentaerythritol | 5:1 | 91 |
| BTDA | Ethylene Glycol | 3:1 | 84 |
| BTDA | Glycerol | 4:1 | 89 |
| BTDA | Pentaerythritol | 5:1 | 106 |

PMA = Pyromellitic anhydride
BTDA = 3,3',4,4'benzophenone tetracarboxylic acid dianhydride To control (ie not pretanned) shrinkage temperatures were typically 76°–79° C.

EXAMPLE 13

Depickled sheepskin with a pretan offer of 25% on pickled weight of BTDA/pentaerythritol (4:1) product. Following retannage with aluminium sulphate and splitting into three layers the following shrinkage temperatures (° C.) were obtained:

| Grain layer | Centre layer | Flesh layer | Whole skin | Whole skin after 6 hr dye bath test |
|---|---|---|---|---|
| 118 | 101 | 96 | 99 | 94 |

Retannage of the pretanned product with basified chromium sulphate gave leather with a Ts of 124° C. compared with 105° C. for skin tanned with the basified chromium sulphate alone.

EXAMPLE 14

Depickled sheepskin with pretan offer of 32% on pickled weight of the PMA/pentaerythritol (4:1) product, Following retannage with aluminium sulphate the following shrinkage temperatures (° C.) were obtained,

| Whole Skin | Whole skin after 6 hr dye bath test |
|---|---|
| 102 | 98 |

EXAMPLE 15

Both depickled sheepskin and intestine were pretanned with a 25% offer on pickled weight of a TMA/pentaerythritol (4:1) product. Following retannage with aluminium sulphate masked with 0.33 mole disodium phthalate per mole of $Al_2O_3$ the following shrinkage temperatures (° C.) were obtained:

| Sheep Intestine | Sheepskin |
|---|---|
| 101 | 97 |

Typically the control (ie, no pretannage) masked aluminium tannage shrinkage temperature was 86° C.,

EXAMPLE 16

EXAMPLE OF WHOLE SKIN TANNAGE

Sheepskin pelts (1+½, drained pickled weight=600 g) were depickled in sodium chloride and sodium acetate to pH 4.8 and rinsed.

The 1½ pelts were then pretanned with the BTDA/pentaerythritol (4:1) product to a final pH of 2.8 following overnight treatment. The skins were washed and they were white with the feel and appearance of leather.

The 1½ pretanned pelts plus control pickled ½ skin were then tanned with phthalate masked aluminium sulphate plus sodium chloride to a final pH of 3.97. They were fatliquored (treated with emulsified softening oils) and dried to form a soft white leather.

Ts after retannage of pretanned ½ skin=99° C.

Ts after aluminium tannage of control ½ skin=74° C. (ie no pretannage).

Finally, it is to be understood that various other modifications and/or alterations may be made without departing from the spirit of the present invention as outlined herein.

We claim:

1. A method of tanning skin or hide, which method includes:
   providing
     a skin or hide;
     an amount of metallic salt, sufficient to have a tanning effect on the skin or hide, wherein the metal is selected from chromium, aluminium, titanium or zirconium; and
     at least one organic polyol ester of gallic acid, trimellitic acid, pyromellitic acid or 3,3',4,4' benzophenone tetracarboxylic acid;
   applying the organic polyol ester to the skin or hide; and
   contacting the skin or hide after it has had the organic polyol ester applied thereto, with the metallic salt in solution for a period sufficient to complex therewith.

2. A method according to claim 1 wherein the metal salt is an aluminium salt, a titanium or a zirconium salt.

3. A method according to claim 1 wherein the metal salt is an aluminium salt.

4. A method according to claim 1 wherein the polyol ester is selected from one or more of the group consisting of, ethylene glycol di(trimellitate), ethylene glycol digallate, ethylene glycol dipryomellitate, polyol esters of ethylene glycol and 3,3',4,4' benzophenone tetracarboxylate, glycerol tri(trimellitate), glycerol trigallate, glycerol tripyromellitate, polyol esters of glycerol and 3,3',4,4' benzophenone tetracarboxylate, pentaerythritol tetra(trimellitate), pentaerythritol tetragallate, pentaerythritol tetrapyromellitate, polyol esters of pentaerythritol and 3,3',4,4' benzophenone tetracarboxylate, sorbitol hexa(trimellitate), sorbitol hexagallate, mannitol hexa(trimellitate), mannitol hexagallate, glucose penta(trimellitate), glucose pentagallate, sucrose octa(trimellitate), sucrose octagallate, lactose octa(trimellitate), and lactose octagallate.

5. A method of tanning a skin or hide, which method includes:
   providing
     a skin or hide;
     an amount of metallic salt, sufficient to have a tanning effect on the skin or hide, wherein the metal is selected from chromium, aluminium, titanium or zirconium; and
     at least one organic polyol ester of trimellitic acid;
   applying the organic polyol ester to the skin or hide; and
   contacting the skin or hide after it has had the organic polyol ester applied thereto, with the metallic salt in solution for a period sufficient to complex therewith.

6. A method according to claim 5 wherein the metallic salt is an aluminium salt, a titanium or a zirconium salt.

7. A method according to claim 5 wherein the metallic salt is an aluminium salt.

8. A method according to claim 5 wherein the polyol ester is selected from one or more of the group consisting of glycerol tri(trimellitate), pentaerythritol tetra(trimellitate), sorbitol hexa(trimellitate), mannitol hexa(trimellitate), glucose penta(trimellitate), sucrose octa(trimellitate), and lactose octa(trimellitate)

9. A method according to claim 1 or claim 5 wherein the metallic ion of said metallic salt is present in an amount of from approximately 0.25% to 10% by weight and the organic polyol ester is present in an amount from approximately 1% to 20% by weight, based on the moist weight of the skin or hide when said skin or hide is green.

10. A tanned hide produced by the method according to claim 1.

11. A tanned hide produced by the method according to claim 1.

* * * * *

UNITED STATES PATENT AND TRADEMARK OFFICE
CERTIFICATE OF CORRECTION

PATENT NO. : 5,501,708

DATED : 03/26/96

INVENTOR(S) : Pojer, et al.

It is certified that error appears in the above-identified patent and that said Letters Patent is hereby corrected as shown below:

On Title page, in [87], line PCT Publication, "WO92/18456" should be --WO92/18457--.

In column 1, line 4, "PCT/au92/00154" should be --PCT/AU92/00154--.

In column 4, before line 20, insert --where--.

Signed and Sealed this

Twenty-fourth Day of September, 1996

Attest:

BRUCE LEHMAN

*Attesting Officer*   *Commissioner of Patents and Trademarks*